United States Patent [19]

Block

[11] Patent Number: 4,662,898

[45] Date of Patent: May 5, 1987

[54] INCREASING THE TEMPERATURE OF THE EXIT GAS FROM THE EXIT GAS WASHER IN THE PREPARATION OF PHTHALIC ANHYDRIDE

[75] Inventor: Ulrich Block, Ludwigshafen, Fed. Rep. of Germany

[73] Assignee: BASF Aktiengesellschaft, Fed. Rep. of Germany

[21] Appl. No.: 775,346

[22] Filed: Sep. 11, 1985

[30] Foreign Application Priority Data

Sep. 12, 1984 [DE] Fed. Rep. of Germany ....... 3433402

[51] Int. Cl.$^4$ .............................................. B01D 47/00
[52] U.S. Cl. .......................................... 55/84; 55/82; 261/150; 562/412
[58] Field of Search ................... 55/82, 83, 84, 89, 85, 55/222; 261/150; 562/412, 408

[56] References Cited

U.S. PATENT DOCUMENTS

| | | | |
|---|---|---|---|
| 2,455,314 | 11/1948 | Pietzsch | 55/82 |
| 3,880,622 | 4/1975 | Howell | 55/222 |
| 3,930,803 | 1/1976 | Winter | 55/84 |
| 4,252,772 | 2/1981 | Way | 55/82 |
| 4,277,453 | 7/1981 | Aiken et al. | 55/82 |
| 4,300,920 | 11/1981 | Grove | 55/84 |

FOREIGN PATENT DOCUMENTS 2039457  11/1978  United Kingdom .

*Primary Examiner*—Bernard Nozick
*Attorney, Agent, or Firm*—Keil & Weinkauf

[57] ABSTRACT

The temperature of the exit gas from the gas washer in the preparation of phthalic anhydride by catalytic oxidation of naphthalene or o-xylene with air is increased by a method in which flue gas from the combustion furnace for residues is mixed with the exit gas before the latter emerges into the atmosphere.

3 Claims, 1 Drawing Figure

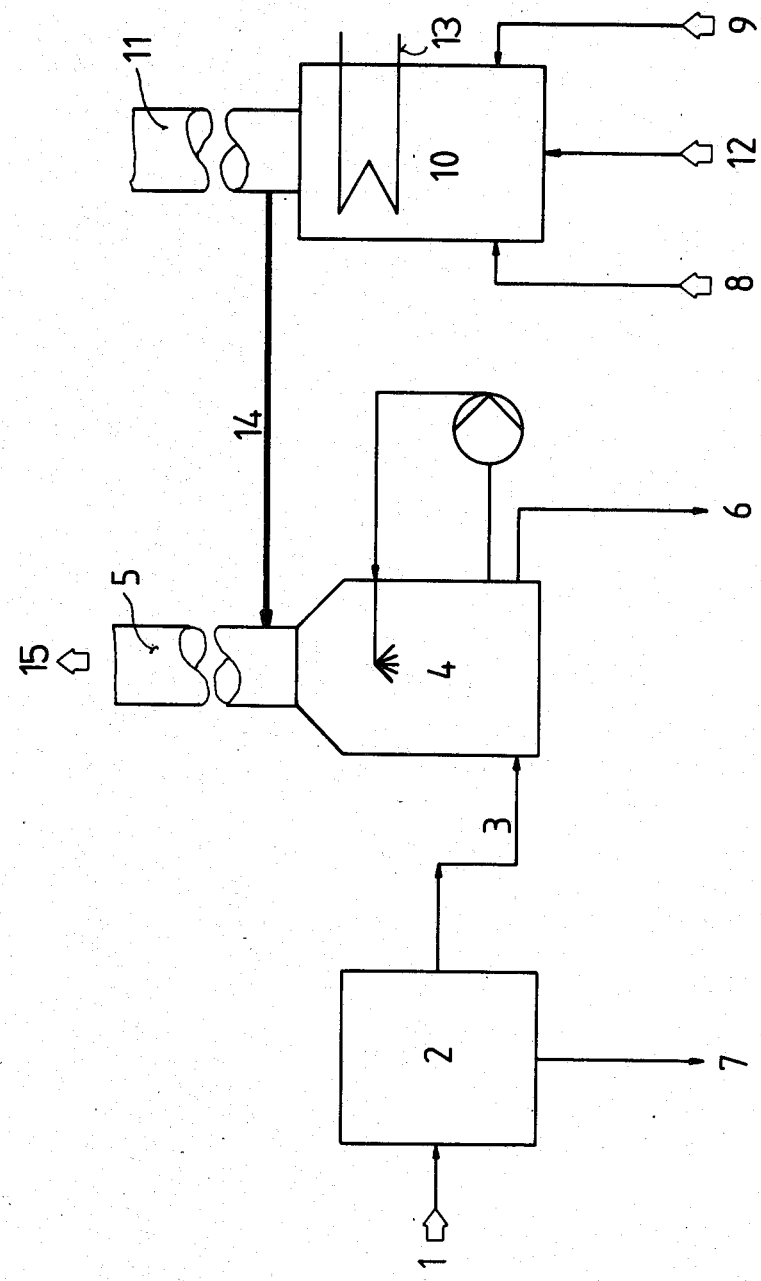

INCREASING THE TEMPERATURE OF THE EXIT GAS FROM THE EXIT GAS WASHER IN THE PREPARATION OF PHTHALIC ANHYDRIDE

The present invention relates to a method for increasing the temperature of the exit gas from the exit gas washer (referred to as exit gas below) in the preparation of phthalic anhydride (PA) by catalytic oxidation of naphthalene or o-xylene with air.

In the process for the preparation of PA by catalytic oxidation of naphthalene or o-xylene with air, as described in the reference work Ullmanns Encyklopädie der technischen Chemie, 4th edition, volume 18, pages 526–532, the exit gas obtained after the wash with wash solution is at 30°–50° C. This exit gas passes through a chimney and into the atmosphere. The low temperature of the exit gas on the one hand necessitates a very high chimney owing to the small thermal advantage, while on the other hand the temperature falls below the dew point as the exit gas is cooled in the chimney, with the result that drops are deposited from the chimney.

To overcome these disadvantages, the temperature of the exit gas can be increased by a method in which some of the hot, untreated exit gas is taken off upstream of the exit gas washer and combined with the colder, treated exit gas downstream of the exit gas washer. However, the consequence of this is that partially untreated gas, which pollutes the environment, passes into the atmosphere. Heating the exit gas stream by means of steam-heated preheaters or oil-fired or natural gas-fired hot gas generators is also disadvantageous, owing to the high energy consumption (cf. Zeitschrift Energie, 33rd year, No. 12, December 1981, pages 404–407).

It is an object of the present invention to increase the temperature of the exit gas.

We have found that this object is achieved, in accordance with the invention, if flue gas from the combustion furnace for residues is mixed with the exit gas before the latter emerges into the atmosphere.

The exit gas and the flue gas from the combustion furnace, in which the low-boiling impurities and the high-boiling residues from the PA and maleic anhydride distillation units are burned, are obtained in a ratio of from 20:1 to 5:1 in the process for the preparation of PA. This ratio is dependent on the specific embodiment of the process and has no influence on the effectiveness of the present invention. The flue gas is at from 500° to 800° C., or from 500° to 200° C. in the case of heat utilization. By mixing the flue gas with the exit gas stream, the temperature of the exit gas is increased by from 10° to 100° C., depending on the ratio of the exit gas to the flue gas and on the temperature of the flue gas. This increase in temperature is sufficient to convert the exit gas from the steam-saturated state to the superheated state, with the result that deposition of drops from the chimney is prevented. Moreover, a greater thermal advantage of the exit gas leads to a lower chimney. Hence, it is desirable to mix all the flue gas with the exit gas, which would make it possible to dispense with the chimney of the combustion furnace, constituting a further advantage of the present invention.

An embodiment of the process according to the invention is illustrated in the drawing and described below. The drawing shows a simplified flow chart of the process.

In the flow chart of the process, the reaction gas 1 which emerges from the reactor and is then cooled to about 180° C. is passed into the separator 2, in which impure PA is deposited in solid form. The gas stream 3, which is cooled to about 50° C. in the separator, is fed to the exit gas washer 4, where the gas stream is purified by washing with water and is released into the environment via the chimney 5, while the aqueous maleic acid obtained during the wash is removed from the exit gas washer as stream 6, from which pure maleic anhydride is obtained in a conventional manner. The impure PA is melted in the separator and taken off as stream 7, from which pure PA is obtained in a conventional manner. The low-boiling impurities 8 and high-boiling residues 9 obtained from the apparatuses for working up the product to give pure PA and pure maleic anhydride are fed to the combustion furnace 10 with the associated chimney 11, and are burned there with the addition of air 12 for combustion. Advantageously, a heat exchanger 13 for recovering heat is located in the combustion furnace 10. Some of the flue gas from the combustion furnace, as stream 14, is mixed with the exit gas stream 15. After the mixing procedure, this exit gas stream emerges in the atmosphere at the higher temperatures according to the invention, ie. at from 40° to 150° C.

I claim:

1. A method for increasing the temperature of an exit gas from an exit gas washer from the preparation of phthalic anhydride by catalytic oxidation of a naphthalene or o-xylene with air, wherein flue gas from a combustion furnace for residues from the burning of phthalic anhydride and maleic anhydride distillation impurities and residues is mixed with the exit gas before the latter emerges into the atmosphere.

2. A method as defined in claim 1, wherein only a portion of the flue gas is mixed with the exit gas.

3. A method as defined in claim 1, wherein all the flue gas is mixed with the exit gas.

* * * * *